(12) United States Patent
Wuestemann et al.

(10) Patent No.: US 8,983,807 B2
(45) Date of Patent: Mar. 17, 2015

(54) METHOD FOR DESIGNING A BONE MORPHOLOGY BASED HIP SYSTEM

(75) Inventors: Thies Wuestemann, Nyack, NY (US); Adam Bastian, Chester, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 492 days.

(21) Appl. No.: 13/358,695

(22) Filed: Jan. 26, 2012

(65) Prior Publication Data

US 2013/0197866 A1 Aug. 1, 2013

(51) Int. Cl.
*G06F 17/50* (2006.01)
*A61B 17/15* (2006.01)
*A61F 2/38* (2006.01)
*A61B 5/00* (2006.01)

(52) U.S. Cl.
CPC ............ *A61B 17/155* (2013.01); *A61F 2/3859* (2013.01); *A61B 5/4528* (2013.01)
USPC .......................................................... 703/1

(58) Field of Classification Search
None
See application file for complete search history.

(56) References Cited

U.S. PATENT DOCUMENTS

| | | |
|---|---|---|
| 4,310,931 A | 1/1982 | Muller |
| 4,822,365 A | 4/1989 | Walker et al. |
| 4,936,862 A | 6/1990 | Walker et al. |
| 5,007,936 A | 4/1991 | Woolson |
| 5,360,446 A | 11/1994 | Kennedy |
| 5,776,204 A | 7/1998 | Noble et al. |
| 6,944,518 B2 | 9/2005 | Roose |
| 7,749,278 B2 | 7/2010 | Frederick et al. |
| 2011/0035192 A1 | 2/2011 | Kisanuki et al. |

OTHER PUBLICATIONS

Kaneuji et al. Three-Dimensional Morphological Analysis of the Proximal Femoral Canal, Using Computer-Aided Design System, in Japanese Patients with Osteoarthrosis of the Hip J Orthop Sci, 5:361-368, 2000.*
Casper et al. Morphology of the Proximal Femur Differs Widely with Age and Sex: Relevance to Design and Selection of Femoral Prostheses Wiley Online Library, Jan. 3, 2012.*
Muller et al. Influence of Minimally Invasive Surgery on Implant Positioning and the Functional Outcome for Medial Unicompartmental Knee Arthroplasty Journal of Arthroplasty vol. 19 No. 3, 2004.*

(Continued)

*Primary Examiner* — Omar Fernandez Rivas
*Assistant Examiner* — Cuong Luu
(74) *Attorney, Agent, or Firm* — Lerner, David, Littenberg, Krumholz & Mentlik, LLP

(57) ABSTRACT

A method of designing a group of femoral implants from three-dimensional images of femurs from a patient population greater than 100. A boundary between cortical and cancellous bone is defined in each of the images. A longitudinal axis of the femur is defined centered within the boundary. The width of the boundary is measured in a direction perpendicular to the axis at multiple cross-sections along the longitudinal axis spaced less than 20 mm. At least five (5) different size implants for implantation in a noncortical bone area of the femur are designed based on the measured widths. At least one area of the proximal femoral component boundary is designed where the implant outer surface is sized to be within 2 mm of the cortical bone. The proximal dimensions of the at least five implants are sized to provide the fit within 2 mm in 95% of the femurs from the population.

19 Claims, 10 Drawing Sheets

(56) References Cited

OTHER PUBLICATIONS

Carter et al. Determination of Accuracy of Preoperative Templating of Noncemented Femoral Prostheses Journal of Arthroplasty vol. 10 No. 4, 1995.*

Aamodt et al. Determination of the Hounsfield Value for CT-Based Design of Custom Femoral Stems British Editorial Society of Bone and Joint Surgery, vol. 81-B, No. 1 Jan. 1999.*

Bo et al, Journal of Orthopaedic Science, 2, pp. 301-312, 1997.

De la Torre BJ et al, 10 years results of an uncemented metaphyseal fit modular stem in elderly patients, Indian Journal of Orthopaedics, 45(4), pp. 351-358, Jul.-Aug. 2011.

Dorr et al, Bone, 14, pp. 231-242, 1993.

Husmann et al, Journal of Arthroplasty, vol. 12, No. 4, pp. 444-450, 1997.

Khang et al, Clinincal Orthopaedics and Related Research, No. 406, pp. 116-122, 2003.

Laine et al, Journal of Arthroplasty, vol. 15, No. 1, pp. 86-92, 2000.

Noble et al, Clinical Orthopaedics and Related Research, No. 235, pp. 148-165, 1988.

Rubin et al., Journal of Bone and Joint Surgery, vol. 74-B, No. 1, pp. 28-32, Jan. 1992.

Umer et al., Journal of Orthopaedic Surgery, 18(3), pp. 279-281, 2010.

* cited by examiner

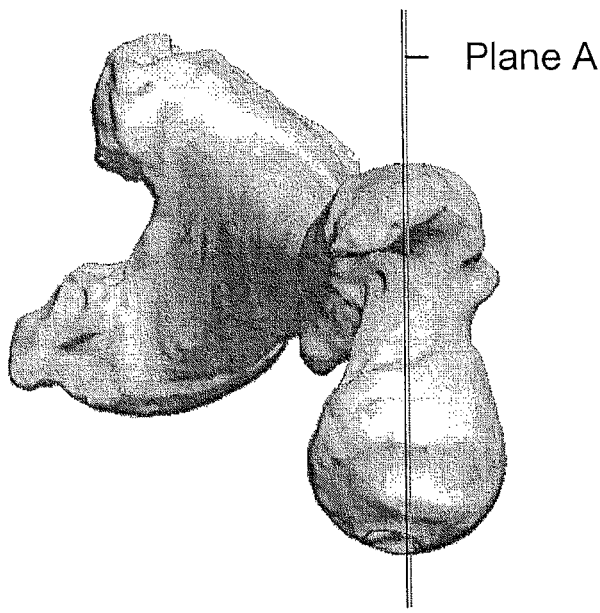
FIG. 3
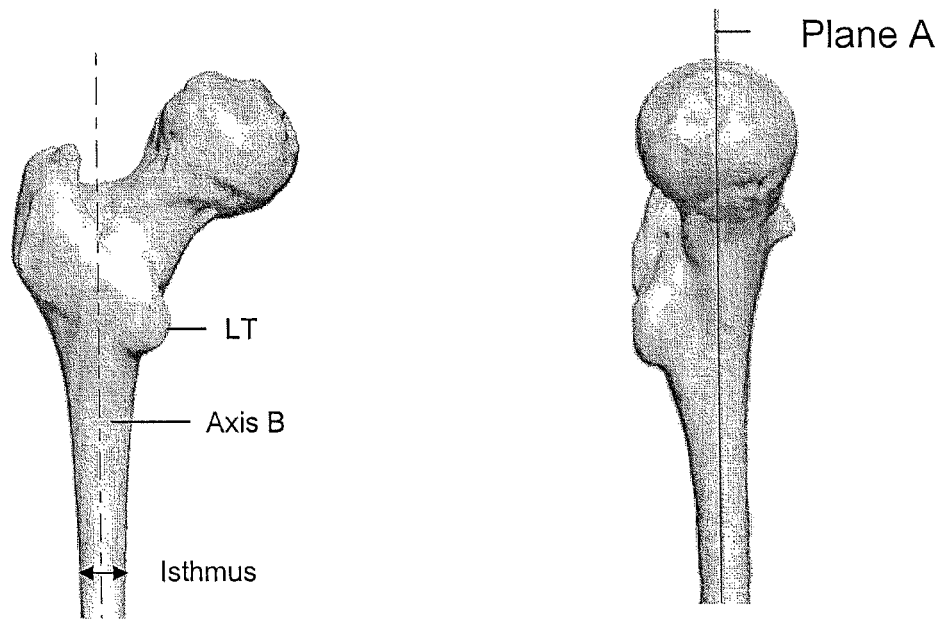
FIG. 5
FIG. 4

METHOD FOR DESIGNING A BONE MORPHOLOGY BASED HIP SYSTEM

BACKGROUND OF THE INVENTION

This invention relates to a method of using bone morphology data to design a family of prosthetic hip implants.

The femoral fit of a prosthetic hip stem component is a key factor for the long term success of a cementless total hip replacement. Traditionally, hip stems have been designed based on predicate clinical data and limited bone morphology data. Numerous studies have analyzed the femur bone morphology. For example, (1) Noble et al., Clinical Orthopaedics and Related Research, 1988; (2) Husmann et al., Journal of Arthoplasty, 1997; (3) Laine et al., Journal of Arthoplasty, 2000; (4) Dorr et al., Bone, 1993; (5) Khang et al., Clinical Orthopaedics and Related Research, 2003; (6) Bo et al., Journal of Orthopaedic Science, 1997. However, a method to utilize bone morphology data for new implant designs has not been developed.

Because bone geometries vary from person to person (and may also vary with age), typical orthopeadic implants are often offered as part of a set or series of different sized implants. Typically, implant sets are created by first designing one size of implant and then scaling that implant in a proportional manner to define the geometries of the other implant sizes (e.g., increasing the width of the elongated insertion region by a uniform amount along the entire length of the stem).

Typical implant system growth does not accurately reflect the geometries of different bone sizes. Larger femurs, for example, are not simply bigger versions of smaller femurs. For instance, it has been discovered that proximal portions of the medullary canal (some or all of which may be referred to as the metaphysis) may "grow" at a greater rate than distal portions (some or all of which may be referred to as the diaphysis) as femoral size increases. Thus, femoral hip stem sets that grown the proximal portion at the same rate as the distal portion from size to size do not necessarily reflect the actual geometries of the various sizes of femurs. Thus, implant sets made in accordance with traditional methodologies may, in some cases, fit poorly when installed, and may lead to implant failure for the reasons discussed above or for other reasons.

U.S. Pat. No. 7,749,278 discloses a hip stem family which has a constant medial portion and an increasing lateral portion (see FIG. 1A).

This invention describes a method to systematically utilize bone morphology data for the development of new hip implant designs. The method is defined in seven (7) steps. (see FIG. 1C.)

BRIEF SUMMARY OF THE INVENTION

The invention relates to a method that systemically utilizes femoral bone morphology data to develop a hip stem design having planar anterior and posterior sides that achieves a tight fit to the femoral canal in the proximal region, with avoiding distal contact only, throughout a complete range of implant sizes, for example, eight (8) sizes. The fit of the stem is determined by several ratios of medial-lateral measurements within the femoral canal. The fit of an implant design can be quantified in proximal and distal bone engagement, proximal bone engagement only and distal bone engagement only in relation to a bone morphology data set and allows iterative improvements of a shape of a hip stem design. The method of the present invention changes the location of both the medial and lateral bone contacting surfaces of the implant with respect to a longitudinal central axis.

A database has been developed containing three dimensional computer tomography (CT) scans obtained from the femoral bones of well over one hundred individuals. The CT scan slice thickness and pixel size of each individuals are 1 mm or less which allows high accuracy measurements. Patient specific data such as gender, weight, height, and ethnicity are associated with each data set. The proximal-distal location of the hip stem implantation is such that the medial proximal end of the stem is located at a femur resection level located 20 mm proximal of the lesser trochanter.

Various aspects of the invention are achieved by a method of designing a group of femoral implants for implantation into a population of patients which includes obtaining three-dimensional images of femur from each patient of a population of patients numbering greater than 100 and preferably greater than 500. The defining a boundary between cortical and cancellous bone in each of the images. A longitudinal axis of the femur geometrically centered within the boundary is defined as the width of the boundary in a direction perpendicular to the axis is measured at multiple cross-sections along the longitudinal axis spaced less than 20 mm apart along the longitudinal axis. At least five (5) different size implants for implantation in a noncortical bone area of the bone are defined based on the measured widths. The stem is designed to produce a line to line fit with bone as near as possible. At least one area of the proximal femoral boundary is defined where the implant outer surface is sized to be within 2 mm of the cortical bone. The proximal dimensions of the at least five implants are revised based on the data to provide the desired fit within 2 mm in 95% of the femurs from the population. The cross-sections are preferably measured in the medial-lateral (M-L) direction across the femur. Alternately, the cross-sections are measured in the anterior-posterior (A-P) direction across the femur. The method includes aggregating the cross-sectional data from the images to create an average stem profile for each of the at least five sizes of stems prior to revising the size of each stem to provide the fit within 2 mm of cortical bone proximally. Additional femoral component stems sizes are added until 95% of the medial proximal cortical boundary cross-sections match a medial proximal stem cross-section within 2 mm. The M-L or A-P cross-sections may be taken at between 10 mm and 20 mm above a femur lesser trochanter to the isthmus area of the femur at 10 to 20 mm intervals. A proximal cross-section of the femoral stem is located within 2 mm of the medial cortical bone and, optimally, a cross-section of the cortical bone boundary at between 60 and 80 mm distal to the lesser trochanter of the femur is within 2 mm of the distal femoral stem. The boundary between cortical and cancellous bone in the CT images is determined by a value of 500 Hounsfeld units.

Another aspect of the invention is achieved by a method of designing a group of prosthetic femoral implants for implantation into a population of patients including obtaining three-dimensional X-ray data (CT) of a femur from each patient in a population of patients numbering greater than 100. Patient specific data, including gender, weight, and height is associated with each femur. A first boundary between cortical and cancellous bone and a second boundary between bone and a marrow canal is defined in each femur. An anterior-posterior (A-P) plane and a longitudinal axis centered in the isthmus and on the A-P plane is located in each femur. Cross-sections in a medial-lateral plane through the longitudinal axis to the boundary between the cancellous and cortical bone are measured along planes from a location on each femur 20 mm above the lesser trochanter to 130 mm below the lesser trochanter at 10 mm increments. A proximal cross-section is defined on each of the femurs 10 mm above the lesser trochanter and a distal cross-section is defined 60 mm below the lesser trochanter. At least 5 femoral implant sizes are selected having proximal cross-sections which match the defined proximal cross-section within 2 mm for 95% of the femurs based on the patient population.

The anterior and posterior sides of the implant may be flat and taper towards the central axis on moving distally.

BRIEF DESCRIPTION OF THE DRAWINGS

FIG. 3 is a proximal to distal view of the femur showing an anterior-posterior (A-P) plane (A) bisecting the femoral neck and the medial calcar in the proximal region of the cancellous bone geometry;

FIG. 4 shows the plane A of FIG. 3 viewed medially to laterally;

FIG. 5 shows an axis on the a-p plane of FIGS. 3 and 4 bisecting the proximal area of the femur and centered within the isthmus (defined as the point of minimum cross-sectional area of the medullary canal) defining the typical orientation of the stem of the prosthetic femoral component in the femoral canal;

FIG. 9 shows a femoral component stem with a close fit proximally and distally, FIG. 10 shows a femoral component with a close fit proximally and FIG. 11 shows a femoral component with a tight fit distally;

DETAILED DESCRIPTION

Figure 1A:
FIG. 1A shows prior art femoral component stems having a constant medial shape and enlarging laterally to provide increasing stem sizes.
Figure 1B:
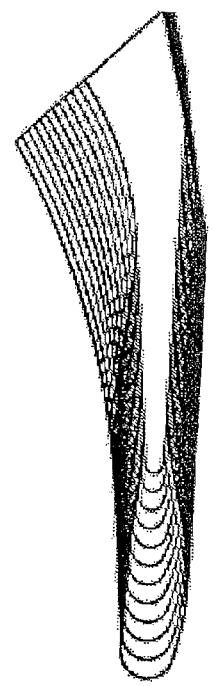
FIG. 1B shows a series of hip stem sizes produced by the design method of the present invention.
Figure 1C:
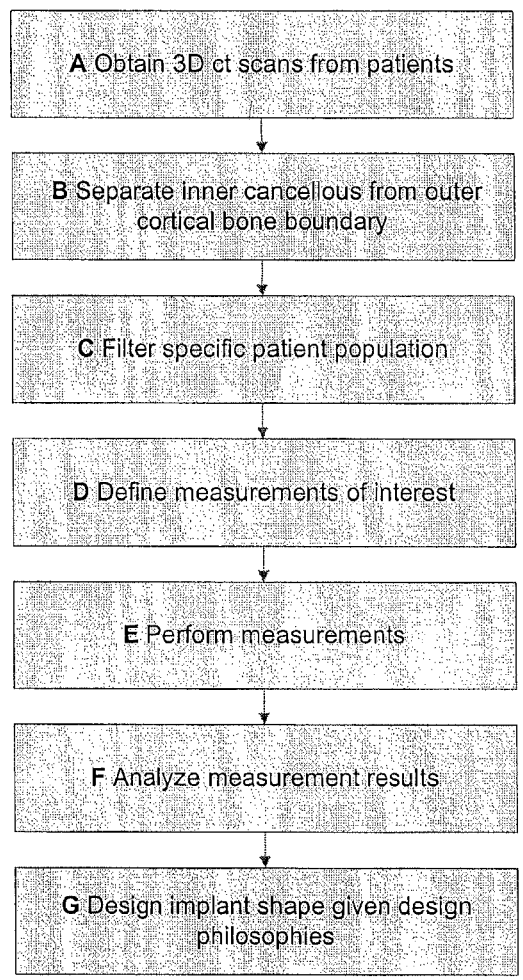
FIG. 1C is a flowchart outlining the general steps in designing a prosthetic bone implant such as a prosthetic femoral component, from a population of patient CT data.

Referring to FIG. 1C there is shown the method for utilizing bone morphology data for the development of a family of femoral component designs. In step A CT scans of the femurs from at least 100 different patients are inputted into a database. In step B the boundary between the inner cancellous bone and the outer cortical bone is determined. In step C a desired patient population, for example a female population, is chosen and the data filtered for this population. In step D, measurements of interest are determined which measurements are generally perpendicular to the anatomic axis of the femur. In step C measurements are determined at increments along the anatomic axis of each femur and in step F are analyzed to determine groupings for use with a single femoral component. Finally in step G, a femoral component's shape is designed based on a given design philosophy such as proximal femoral fit for example within two millimeters of the prepared canal for the largest grouping of patients possible for the single femoral component.

The segmentation of cortical, cancellous and marrow boundaries is performed with the CT data by the software in Step B. A value of 500 Hounsfield units should be used to define the boundary between cortical and cancellous bone.

Based on the specific area of interest, the data is filtered by criteria such as specific age ranges, genders and height ranges.

Figure 2:
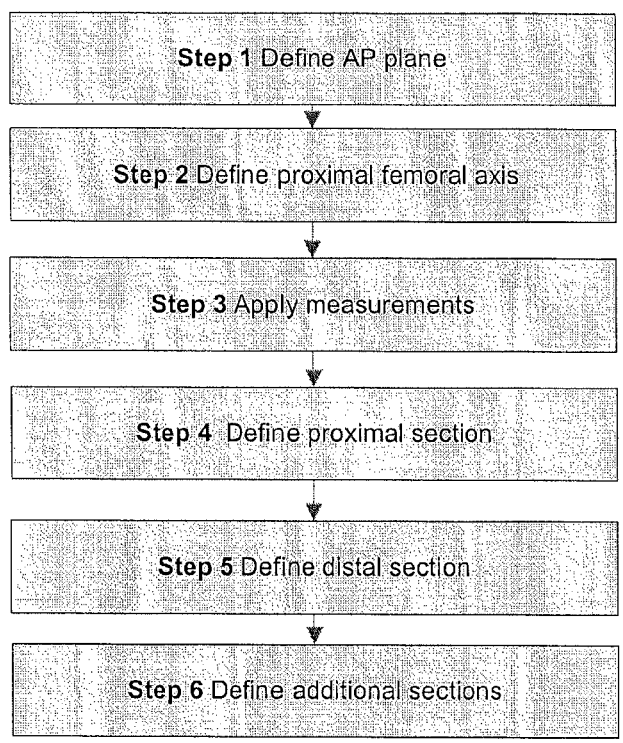
FIG. 2 is a flowchart showing the specific steps within step E of FIG. 1C used in performing measurements to be used in designing a prosthetic femoral component.

Measurements of interest of each femur in the database of femurs are made by the software in step D. This process is separated into six steps, as shown in FIG. 2.

Step 1—Define an Anterior-Posterior (AP) plane (plane A) that bisects the femoral neck and the medial calcar in the proximal region of the cancellous bone geometry (see FIG. 3). The orientation of the plane A matches the orientation of a hip stem prosthesis in the femoral canal. A hip stem prosthesis is typically implanted following the orientation of the medial calcar to match the native anteversion of the femoral neck as close as possible.

Step 2—Define an axis (axis B) on the plane A that bisects the proximal area of the femoral bone. (see FIGS. 4 and 5.) In order to consider the placement of a conventional length hip stem, the axis is defined by the area from the isthmus (defined as the point of minimum cross-sectional area of the medullary (IM) canal) to the lesser trochanter (LT). The axis B is centered in the IM canal at the isthmus. The direction of the axis B matches the typical orientation of hip stem prosthesis in the femoral canal. A hip stem prosthesis typically follows the direction of the femoral canal.

Figure 6:
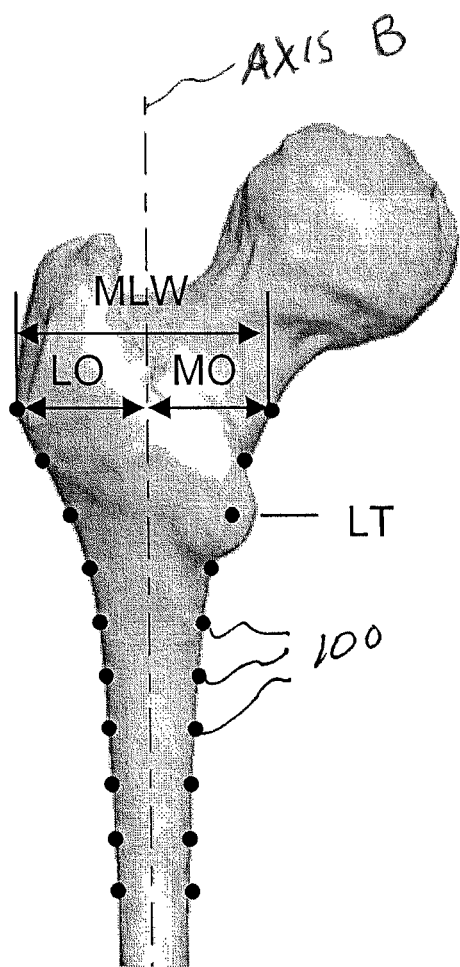
FIG. 6 is a view of the cancellous bone of the femur showing the outline of the cancellous bone developed from the CT scans with the mediolateral width, medial offset and lateral offset from the axes of FIG. 5 in 10 mm increments ranging from 20 mm above the lessor trochanter to 130 mm below the lessor trochanter.

Step 3—Perform and record measurements of the cancellous/cortical bone boundary for the mediolateral width (MLW), medial offset (MO) and lateral offset (LO) in 10 mm increments, ranging from 20 mm above the lesser trochanter to 130 mm below the lesser trochanter for each femur in the database. (see FIG. 6). A predetermined number of cross-sections 100 are utilized as shown in FIG. 6 preferably numbering between 10 and 20.

The measurements are taken along the medial and lateral curvature to capture the complete area where the implant is buried inside the femoral bone. The area depends on the length of the stem and the height of the implantation level.

Figure 7:
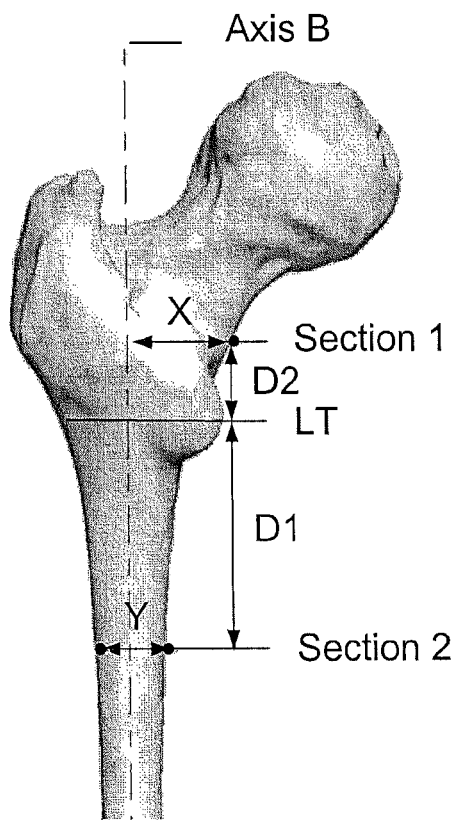
FIG. 7 defines the measurements used to design a prosthetic femoral component.

Step 4—Define a proximal section (Section 1, see FIG. 7) that is proximal in a distance of 10 mm to the lesser trochanter (D2). Measure the distance of the most medial point of the cancellous bone boundary to the axis B (X). The proximal measure is taken perpendicular to axis B.

This measurement is taken in a section where the implant should come into close contact with the cortical bone. A close contact to the cortical bone in the medial proximal area provides loading in a manner that is close to the physiological loading of the natural femoral bone. This avoids stress shielding that could lead to bone atrophy in the proximal area of the stem. See De la Torre B J et al., "10 Years Results of an Uncemented Metaphyseal Fit Modular Stem in Elderly Patients, *Indian Journal of Orthopaedics,* 2011. The specific section is chosen at 10 mm above the lesser trochanter because this section is most important for a close fit to the cortical bone. Additional sections may be performed in this area as specified below in Step 6. Since the implant components typically do not require contact on the lateral side in the proximal area, the proximal section is limited to the medial offset (MO). However, if an implant should have a lateral contact in the proximal area, the mediolateral width should be used for the proximal section.

Step 5—Define a distal section (Section 2, see FIG. 7) that is in a distance of 60 mm distally to the lesser trochanter (D1). Measure the distance of the most medial point of the cancellous bone boundary to the most lateral point of the cancellous bone boundary. The distal measurement is taken perpendicular to the center to axis B.

This measurement is taken in a section where the implant should be guided by the cortical bone to be in neutral alignment. Varus or valgus orientation of the implant component should be avoided. However, the implant should not be in contact with the cortical bone in the distal section and should not provide any contact with the cortical bone in the proximal section. Since the implant components can be in contact on the lateral and medial side in the distal area, the distal section is measured from the medial to the lateral side (mediolateral width MLW). The specific section is chosen at 60 mm below the lesser trochanter because this section is most important for the guidance of the distal section of the bone. Additional sections should be performed as specified in Step 6.

Step 6—Additional sections and ratios may be established to measure the bone morphology in other areas than the sections defined in Step 4 and Step 5. FIG. 6A shows a matrix of different sections that should be measured to analyze the fit of a hip implant. A minimum of 15 sections should be analyzed. The actual number of sections also depends on the actual stem length, implantation height and the given design philosophy. The proximal fit, the proximal to mid region fit, proximal to distal fit, mid region fit, mid region to distal fit and distal fit should be captured in the ratios.

This is because in order to assess the complete fit of the stem, it is necessary to establish a sufficient amount of cross sections and ratios to make sure that all areas of the lateral and medial curvature of the stem are captured. The offsets are measured at the various proximal distal locations from the lesser trochanter.

The measurements should be performed with a software that allows a precise analysis of large quantity of CT scans. The software should automatically perform the measurements by defining them on one template bone. The output should be generated with associated patient characteristics.

Figure 8:
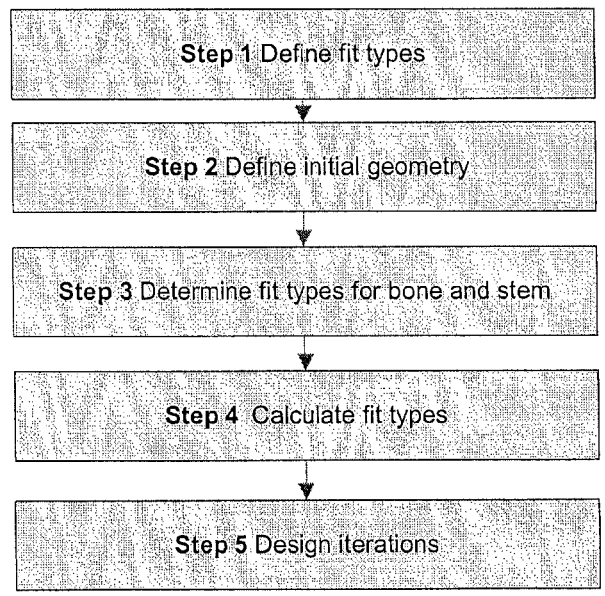
FIG. 8 is a flowchart setting forth steps used in designing the prosthetic femoral component of step F of FIG. 1C based on the measurements of FIG. 7.

Referring to FIG. 8 the measurements of interest are then analyzed. This section is separated into five steps as shown in FIG. 8.

Figures 9, 10, 11:
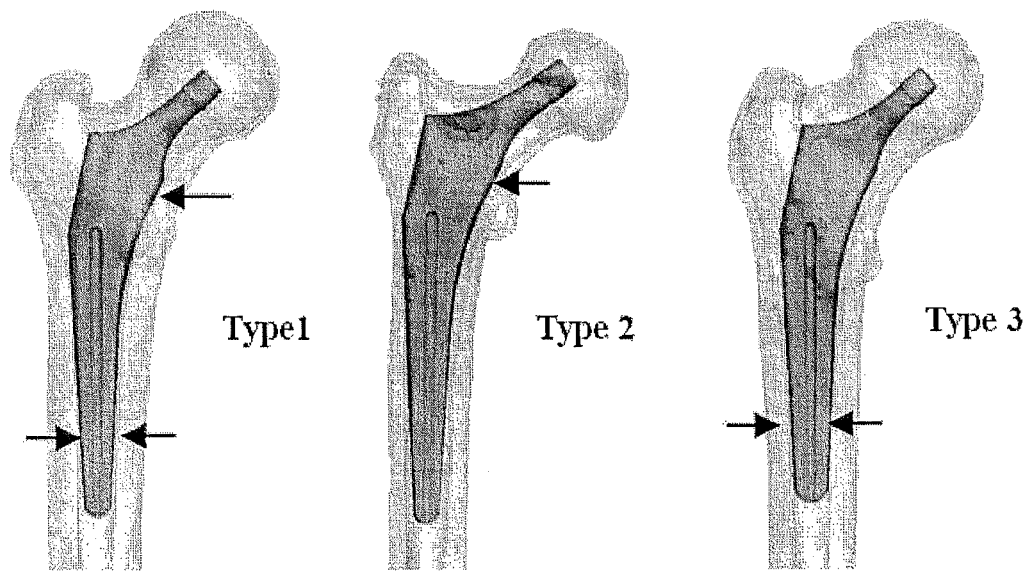
FIGS. 9-11 show three different femoral component design philosophies where

Step 1—In order to assess the fit of a hip implant, the ratio of several sections is analyzed to define fit types. In this example a section that is located 10 mm proximally to the lesser trochanter and a section that is 60 mm distally to the lesser trochanter are analyzed. An engagement of the hip component (contact to cortical bone) occurs distally and/or proximally. The fit of an implant can be classified into three different types. Type 1 (FIG. 9), where there is both proximal and distal engagement, Type 2, proximal engagement only (FIG. 10), Type 3, distal engagement only (FIG. 11) In Type 1 a gap between the implant and the cortical bone can occur either proximally or distally up to a specified limit (z) and still be considered an engagement between the implant and cortical bone. This assumes all the cancellous bone (as defined above) is removed during canal preparation. Z is preferably 2 mm. However, z could be also chosen differently based on the specific design philosophy.

Figures 12, 13:
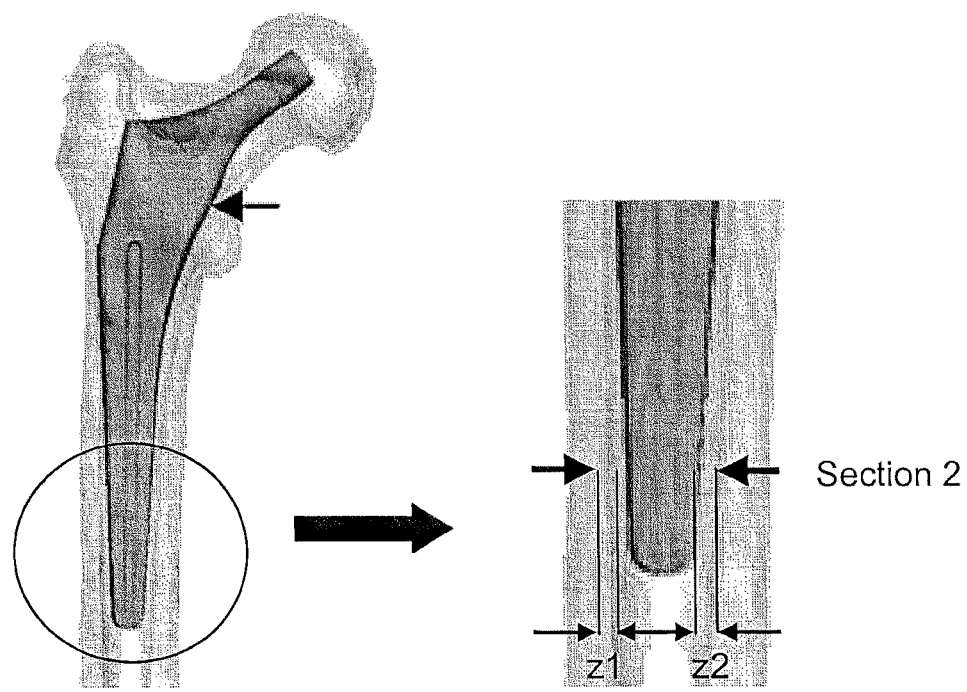
FIGS. 12 and 13 show the distal engagement difference for the prosthetic femoral component of FIG. 11.
Figures 14, 15:
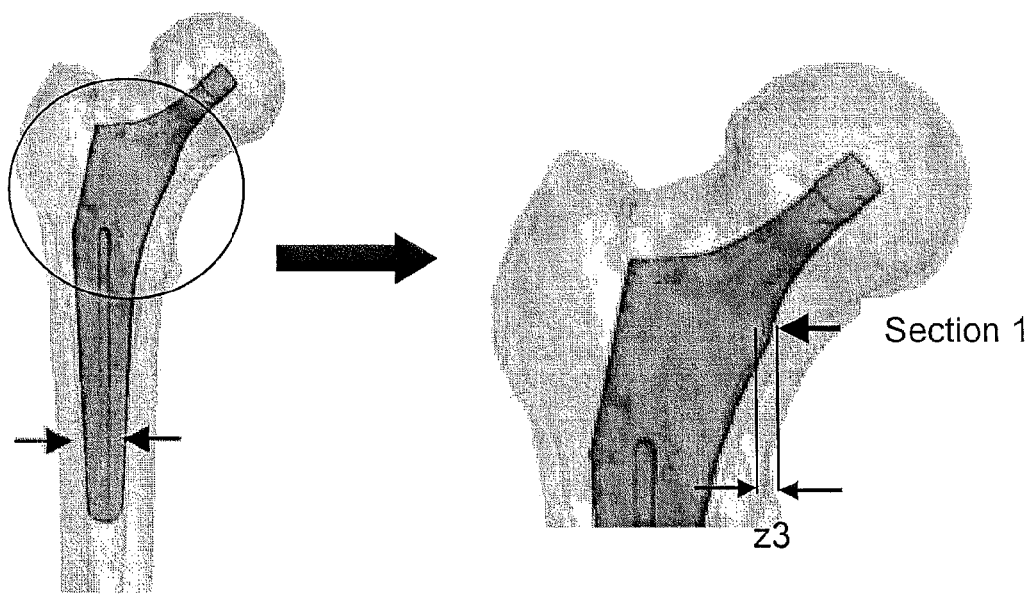
FIGS. 14 and 15 show the proximal engagement difference for the prosthetic femoral component design of FIG. 11.

The distal and proximal engagement differences can be calculated as follows.

$$Z\ distal = (Z1+Z2)/2 \text{(See FIGS. 12 and 12)}$$

$$Z\ proximal\ Z3 \text{(See FIGS. 14 and 15)}$$

Step 2—The initial proximal and distal relationship of a complete family of hip stems (including all, for example, eight (8) femoral component sizes) can be described as a mathematical function. Based on the specific design, it could be a linear or non linear relationship. For example, a linear relationship within a family can be described as:

$$Y_{design} = m * X_{design} + b$$

$Y_{design}$—proximal section length, for example in millimeters for specific size $X_{design}$—distal section in length, for example millimeters for specific size m—slope of the line b—y intercept Most of the prior hip stem designs feature a proximal linear relationship throughout the complete size range. This means that sizes are just scaled up versions of the smallest size. However, a non linear relationship may result into a better fit across the complete size range. For example, a nonlinear relationship among a family of femoral components can be described as a polynomial function of a second order:

$$Y_{design} + a_1 X_{design}^2 + a_2 x + a_3$$

In order to assess the fit of any prototype or actual hip implant design, the data points of the bone morphology data can be compared to the specific proximal distal ratios of the implant designs. To quantify the three types of fit, the following calculations are performed.

Step 3—The fit type for bone and stem is then determined.

Type 1: Proximal and distal engagement $$Y_{bone} + 2\ mm > Y_{design} > Y_{bone} - 2\ mm$$

If the distal width of the subject design "$Y_{design}$" of the stem is no more than 2 mm smaller or larger than the actual bone data "$Y_{bone}$" then it is considered to be a distal and proximal engagement.

Type 2: Proximal engagement $$Y_{design} < Y_{bone} - 2\ mm$$

If the distal width of the subject design "$Y_{design}$" of the stem is 2 mm smaller than the actual bone data " " of the stem is 2 mm smaller than the actual bone data "$Y_{bone}$" then it is considered to be a proximal engagement.

Type 3: Distal engagement $$Y_{design} > Y_{bone} + 2\ mm$$

If the calculated distal width "$Y_{design}$" of the stem is 2 mm larger than the actual bone data x-ray "$Y_{bone}$", then it is considered to be a distal engagement.

Step 4—The fit type is then calculated with the proximal fit within 2 mm required (Type I or II.)

For each bone, the type of fit is calculated for the specific stem design. The actual incidences of fit types are recorded for all bones. Below is an example of how the fit type is calculated for one specific bone.

a) Bone dimensions
$X_{bone}$ 16.98 mm (proximal section)
$Y_{bone}$ 10.32 mm (distal section)
b) Calculated stem dimensions
$Y_{design} 2*X_{bone} - 26.5$ (proximal distal ratio of the picked stem)
$Y_{design} = 2*16.98$ mm$-26.5 = 7.5$ mm
c) Categorize fit type
$Y_{bone} + 2 > Y_{design} > Y_{bone} - 2$ (Type 1: Proximal and distal engagement) 12.32 mm>7.5 mm>8.32 mm is not true
$Y_{design} < Y_{bone} - 2$ (Type 2: Proximal engagement) 7.5 mm<8.32 mm is true
$Y_{design} >>_{bone} + 2$ (Type 3: Distal engagement) 7.5 mm>10.32 is not true
Conclusion: For the specific bone, the stem has a proximal engagement (Type 2)

Figure 16:
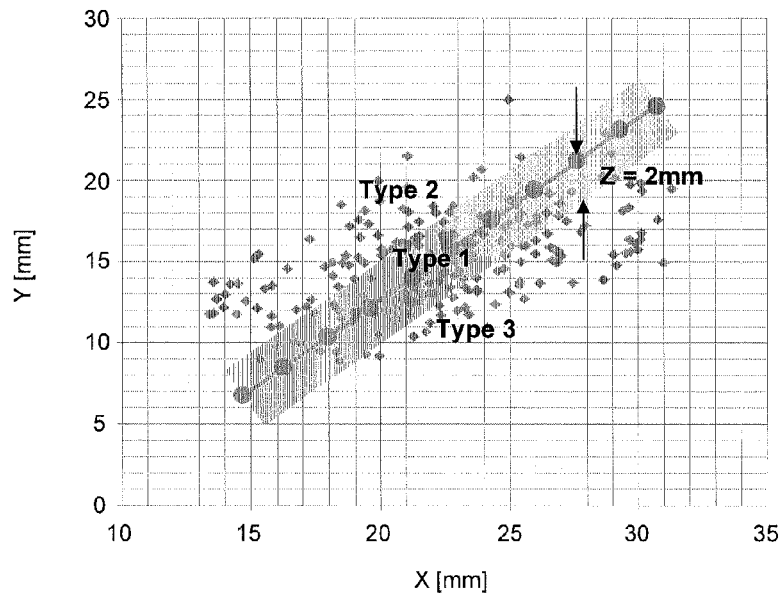
FIG. 16 shows the proximal and distal ratio for an initial prosthetic femoral component design and its correlation to the data of the three types of hip stems shown in FIGS. 9-11.

Step 5—The initial stem design is modified through an interactive process for better fit. FIG. 16 shows an example for proximal and distal bone data overlaid with an initial stem design ratio. The line is representing the distal and proximal ratio of the initial stem design throughout the complete size range. The dots on the line are representing the proximal and distal ratios for specific stem size. Type 1 (proximal and distal engagement) occurs at a band close to the stem design with an engagement different of z. The proximal engagement occurs above Type 1 and distal engagement below Type 1. For this specific example, there is a considerable amount of Type 3 that should be avoided. No more than 5% Type 3 is acceptable.

Figure 17:
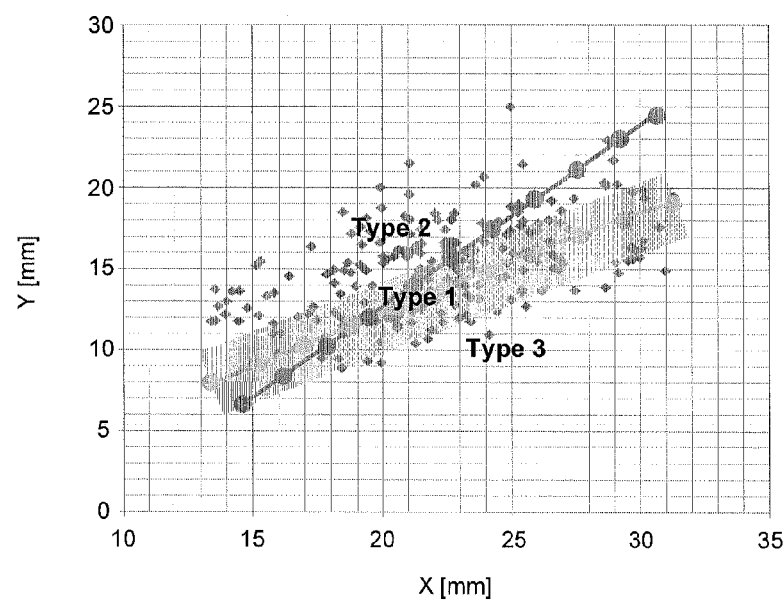
FIG. 17 shows an example for bone morphology data for an optimized stem design, including the proximal and distal ratio for the initial design of FIG. 16 optimized to match the CT data patient population produced a type 1 and type 2 fit.

FIG. 17 shows an optimized stem designed based on minimizing the Type 3 (distal engagement). The proximal and distal relations hip is changed to a polynomial relationship throughout the size range. This allows a balanced ratio through the size range with a minimal amount of Type 3 (distal engagement). The incidences of Type 1, Type 2 and Type 3 can be quantified as described in sections 3 and 4 in order to allow precise optimization of the design. If the design does not meet the objectives of the specific fit types, further optimization throughout step 2 to step 5 is required.

Based on the clinical history of hip implant design and the specific indications of hip replacements, there a multiple design philosophies for hip implant designs. For example, a flat tapered hip stem prosthesis relies primarily on a close proximal fit to the cortical bone in the proximal region, whereas distal fill without proximal engagement should be avoided. A fit and fill prosthesis with larger anterior posterior widths relies more on a proximal and distal fill. In this case, distal reaming is part of the standard practice and more distal fill may be acceptable. The previously described technique allows developing and assessing various design philosophies. The desired proximal and distal ratios can be quantified and optimized for a given design philosophy. The optimization can be done through reiterating a prototype implant shape until the desired fit is achieved that is quantified by the proximal and distal types (1, 2, 3). For example, a flat tapered wedge design should have a large number of type 1 (Proximal and distal fill) and type 2 (Proximal fill), whereas type 1 (distal fill only) should be minimal (less than 5%). In order to achieve these design requirements, it may be necessary to change the design to a size dependent medial curvature. The currently commercially available flat tapered stems feature a single medial curvature. A single medial curvature may not allow an optimized proximal and distal fit with avoiding the distal fill type 3. Also, the above described techniques can be applied to the anterior posterior dimensions of bones and implants as well as circumferential ratio optimizations can be performed.

EXAMPLE

Five stems of the prior art (STD) tapered wedge design similar to FIG. 1 (Accolade® TMZF, Stryker Orthopaedics, Mahwah, N.J.) and the stem of the present invention were implanted into a homogenous set of 10 synthetic femora utilizing large left fourth generation composite femurs (purchased from Sawbones, Pacific Labs, Seattle, Wash.).

The six-degrees-of-freedom (6 DoF) motions of the implanted stems were recorded under short-cycle stair-climbing loads similar to a previous study of press-fit stems.

Minimum head load was 0.15 kN and the maximum varied between 3 Body Weights (BW) and 6 BW. Loading began with 100-cycles of 3 BW and was stepped up to 4 BW, 5 BW and 6 BW for 50-cycles each. Prior to each load increase, 50 cycles of 3 BW loading was applied. This strategy allowed a repeatable measure of cyclic stability after each higher load was applied.

The 6 DoF micromotion data, acquired during the repeated 3 BW loading segments, were reduced to four outcome measures: two stem migrations (retroversion and subsidence at minimum load) and two cyclic motions (cyclic retroversion and cyclic subsidence).

Figure 18:
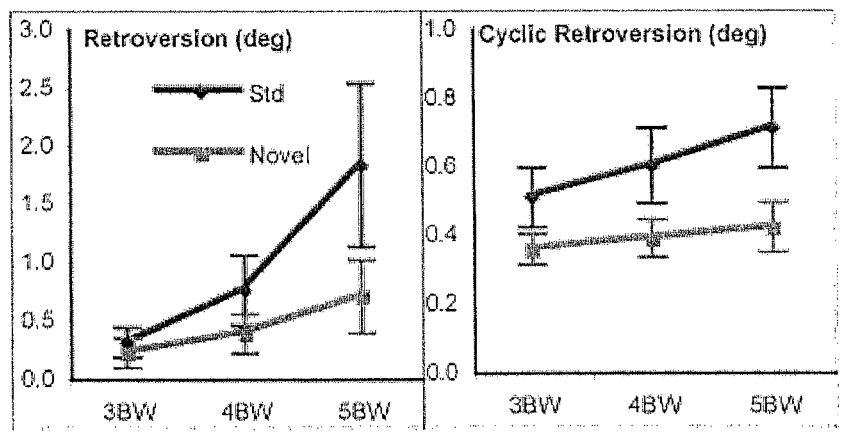
FIG. 18 shows the retroversion migration and cyclic motion for standard (Std) and the femoral stems of the present invention (novel)

With regard to migrations, both stems retroverted under increasing load (p=0.0011, FIG. 18.) Retroversion of the stem of the present invention was significantly smaller than that of the standard tapered wedge stem (p=0.023).

Figure 19:
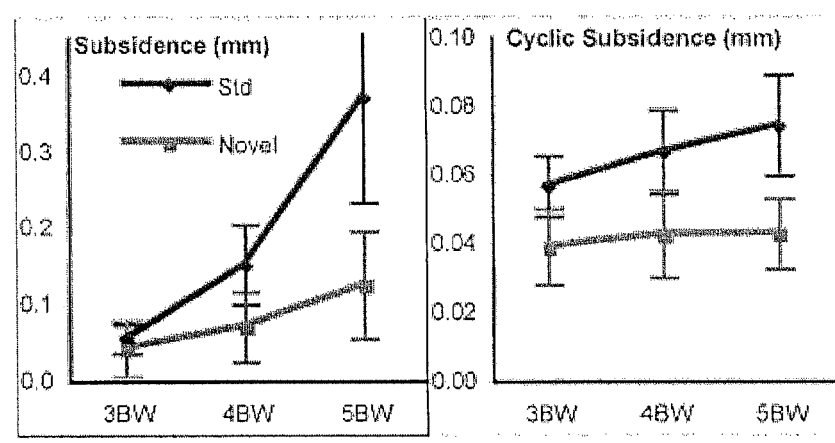
FIG. 19 shows the subsidence migration and cyclic motion for standard (Std) and the femoral stems of the present invention (novel).

The rate of increase in retroversion with increasing load was significantly lower for the stem of the present invention (p=0.026). In addition, both stems subsided under increasing load (p=0.0015, FIG. 19).

Subsidence of the stem of the present invention was significantly smaller than that of the standard tapered wedge stem (p=0.016). The rate of increase in subsidence with increasing load was significantly lower for the stem of the present invention (p=0.022).

With regard to cyclic motions, both cyclic retroversion and cyclic subsidence were significantly lower for the stems of the present invention (p=0.0033 and p=0.0098).

In addition, the rate of increase in cyclic motion was significantly lower for the stems of the present invention for both cyclic retroversion (p=0.0021) and cyclic subsidence (p=0.023).

The tapered stem design of the method disclosed herein has an improved femoral fit. The stem design has a size specific medial curvature that allows more proximal fill than the prior art design. The present stem showed an improved initial stability compared to the prior art. Through optimization of the proximal geometry, a reduced length of the stem can be used without jeopardizing initial stability if a shorter stem is desired.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of designing a group of femoral implants for implantation into a population of patients comprising:
obtaining three-dimensional images of femur from each patient of a population of patients numbering greater than 100;
defining a boundary between cortical and cancellous bone in each of the images;
defining a longitudinal axis of the femur geometrically centered within the boundary;
measuring the width of the boundary in a direction perpendicular to the axis at multiple cross-sections along the longitudinal axis spaced less than 20 mm apart along the longitudinal axis;
defining at least five (5) different size implants for implantation in a noncortical bone area of the bone based on the measured widths;
defining at least one area of the proximal femoral boundary where the implant outer surface is sized to be within 2 mm on a medial side of the cortical bone; and
revising proximal dimensions of the at least five different size implants to provide the fit of the implants within 2 mm on the medial side in 95% of the femurs from the population further comprising aggregating cross-sectional data from the images to create an average stem profile for each of the at least five different size implants prior to revising the size of each stem to provide the fit within 2 mm of cortical bone proximally.

2. The method as set forth in claim 1, wherein the cross-sections are measured in the medial-lateral direction across the femur.

3. The method of claim 1, wherein the cross-sections are measured in the anterior-posterior direction across the femur.

4. The method as set forth in claim 2, wherein additional femoral implants' sizes are added until 95% of the medial proximal cortical boundary cross-sections match a medial proximal stem cross-section within 2 mm.

5. The method as set forth in claim 4, wherein the medial cross-section is taken at between 10 mm and 20 mm above a femur lesser trochanter.

6. The method as set forth in claim 5, wherein the cross-section is measured from the longitudinal axis to the medial cortical bone between 10 mm and 20 mm above the lesser trochanter.

7. The method as set forth in claim 6, wherein a proximal cross-section of the femoral stem is within 2 mm of the medial cortical bone.

8. The method as set forth in claim 7, wherein a cross-section of the cortical bone boundary at between 60 and 80 mm distal to the lesser trochanter of the femur is within 2 mm of the distal femoral stem.

9. The method as set forth in claim 1, wherein the boundary between cortical and cancellous bone in the images is a value of 500 Hounsfeld units.

10. The method as set forth in claim 1 wherein the stem anterior and posterior sides are planar.

11. A method of designing a group of prosthetic femoral implants for implantation into a population of patients, comprising:
obtaining three-dimensional X-ray data of a femur from each patient in a population of patients numbering greater than 100;
associating patient specific data, including gender, weight, and height with each femur;
defining a first boundary between cortical and cancellous bone and a second boundary between bone and a marrow canal in each femur;
defining an anterior-posterior (A-P) plane and a longitudinal axis centered in the isthmus and on the A-P plane in each femur;
measuring cross-sections in medial-lateral planes through the longitudinal axis to the boundary between the cancellous and cortical bone along planes from a location on each femur 20 mm above the lesser trochanter to 130 mm below the lesser trochanter at 10 mm increments;
defining a proximal cross-section on each of the femur 10 mm above the lesser trochanter and a distal cross-section 60 mm below the lesser trochanter;
selecting at least 5 femoral implant sizes having proximal cross-sections which match the defined proximal cross-section within 2 mm for 95% of the femurs from the patient population.

12. The method as set forth in claim 11, further comprising aggregating the cross-sectional data from the images to create an average stem profile for each of the at least five femoral implant sizes prior to revising the size of each stem to provide the fit within 2 mm of cortical bone proximally.

13. The method as set forth in claim 11, wherein the medial cross-section is taken at between 10 mm and 20 mm above a femur lesser trochanter.

14. The method as set forth in claim 13, wherein the cross-section is measured from the longitudinal axis to the medial cortical bone between 10 mm and 20 mm above the lesser trochanter.

15. The method as set forth in claim 14, wherein a proximal cross-section of the femoral stem is within 2 mm of the medial cortical bone.

16. The method as set forth in claim 15, wherein a cross-section of the cortical bone boundary at between 60 and 80 mm distal to the lesser trochanter of the femur is within 2 mm of the distal femoral stem.

17. The method as set forth in claim 11, wherein the boundary between cortical and cancellous bone in the images is a value of 500 Hounsfeld units.

18. The method as set forth in claim 11 wherein the stem anterior and posterior sides are planar and taper inwardly proximally to distally.

19. The method as set forth in claim 11 wherein a distal stem portion is within an average of 2 mm from medial and lateral bone surfaces.

* * * * *